United States Patent [19]

Baudet et al.

[11] 3,993,816

[45] Nov. 23, 1976

[54] HOLLOW FIBER ASSEMBLY FOR USE IN FLUID TREATMENT APPARATUS

[75] Inventors: Jacques Baudet, Roussillon; Michel Rochet, Bron; Michel Salmon, Mions; Bernard Vogt, Caluire, all of France

[73] Assignee: Rhone-Poulenc S.A., Paris, France

[22] Filed: July 10, 1974

[21] Appl. No.: 487,400

[30] Foreign Application Priority Data
July 11, 1973  France .............................. 73.25450

[52] U.S. Cl. .................................. 428/45; 428/81; 428/120; 165/177; 210/22 R; 210/321 R
[51] Int. Cl.² ...................... B32B 3/02; B32B 5/02; B01D 13/00; F28F 3/08
[58] Field of Search ............................... 161/43–44, 161/178; 156/172, 175; 264/45.1, 45.4, 54, 45.3; 210/321, 22–23 R, 321 R; 428/45, 81, 119–120; 165/177

[56] References Cited
UNITED STATES PATENTS

| | | | |
|---|---|---|---|
| 3,228,876 | 1/1966 | Mahon | 210/321 X |
| 3,228,877 | 1/1966 | Mahon | 210/321 X |
| 3,239,002 | 3/1966 | Young | 165/177 X |
| 3,422,008 | 1/1969 | McLain | 210/321 X |
| 3,442,002 | 5/1969 | Geary, Jr. et al. | 210/321 X |
| 3,462,362 | 8/1969 | Kollsman | 210/321 X |
| 3,475,331 | 10/1969 | McLain | 210/321 |
| 3,704,223 | 11/1972 | Dietzsch et al. | 210/22 X |
| 3,884,814 | 5/1975 | Vogt et al. | 210/321 R |
| 3,891,547 | 6/1975 | Chang et al. | 210/321 R |

*Primary Examiner*—Philip Dier
*Attorney, Agent, or Firm*—Cushman, Darby & Cushman

[57] ABSTRACT

An assembly of hollow fibers for use in fluid treatment apparatus and apparatus incorporating such assemblies, in which a primary frame is provided with a central window defined by edges at least two of the opposite edges being thinned down to form hollows. A web of hollow fibers is placed in the hollows and is secured in place, and the fibers secured to one another, by a mass of hardened resin material in at least one of the hollows.

The assemblies are mounted in a container, through which a first fluid is caused to flow, the fluid passing around the fibers and through the windows before leaving the container. The interiors of the hollow fibers are connected to the exterior of the container so that either fluid permeate flows out of the apparatus via the interiors of the fibers or a second fluid is caused to flow through the interiors of the fibers if some form of fluid exchange is desired.

19 Claims, 23 Drawing Figures

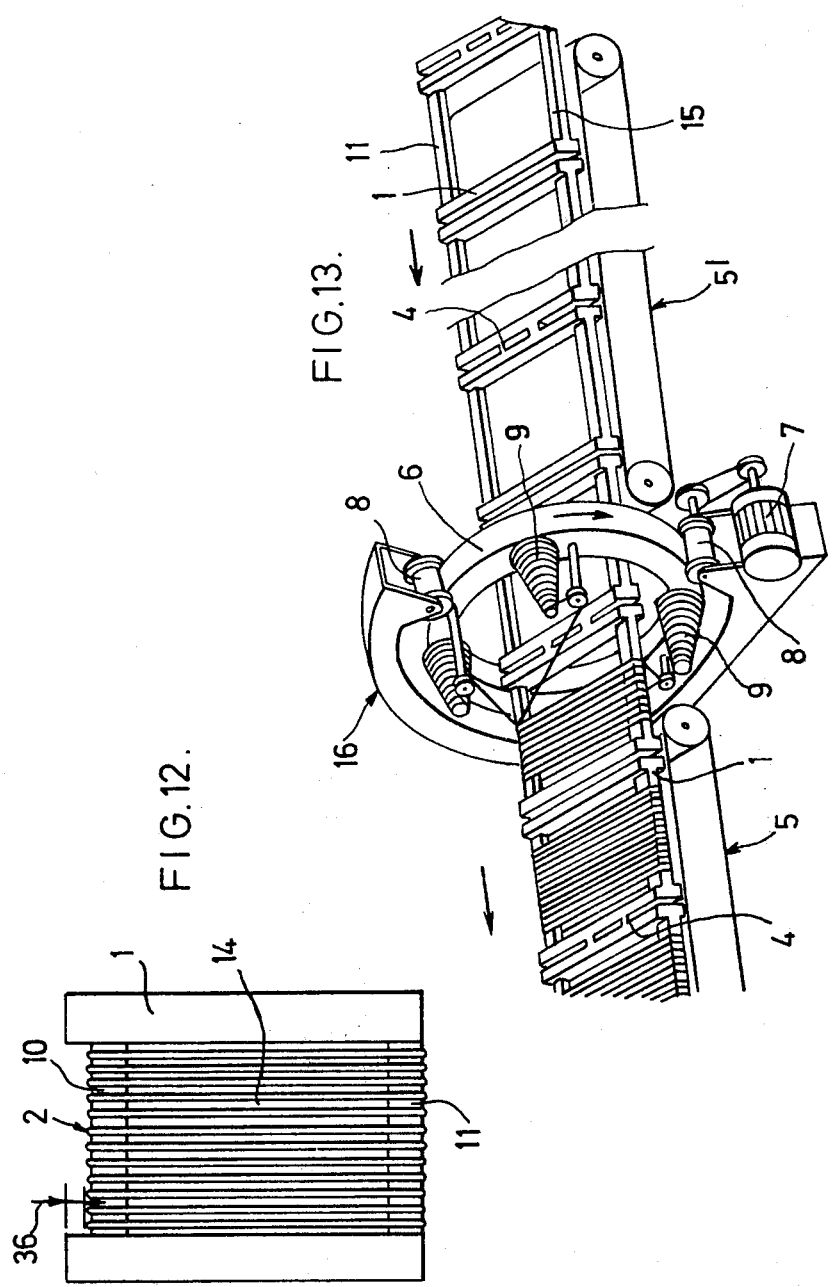

HOLLOW FIBER ASSEMBLY FOR USE IN FLUID TREATMENT APPARATUS

The present invention relates to fluid treatment apparatus employing hollow fibres as well as to assemblies of hollow fibres for use in such apparatus.

The treatment operations considered are essentially exchange operations (dialysis, for example the artificial kidney; direct osmosis; gas-gas exchanges; and liquid-gas exchanges, for example the artificial lung), separation operations (ultra-filtration, reverse osmosis and gas permeation) and even mixing operations. These operations can of course be enriching operations. The invention also includes the use of the apparatuses described in exchange applications such as heat exchange between two fluids, in air humidification and/or air conditioning, and the dissolution of certain gases in liquids (in this case, mixing is involved); furthermore, the majority of these diverse applications fall within the categories of exchange, separation and mixing indicated above.

A separation apparatus with hollow fibres has been described in French Pat. No. 1,547,549 in which these hollow fibres are made into the form of a square of woven fabric placed in a frame, this frame has in its edges, an even number (at least four) of peripheral openings, which are spaced apart opposite one another and are used to allow fluid to flow inside the fibres.

According to the present invention we provide a hollow fibre assembly for use in fluid treatment apparatus, such assembly comprising a primary frame having a central window surrounded by edges, a thinned down portion of at least two of said edges defining at least two hollows, a mass of resin material in at least one of said hollows and a web of hollow fibres extending between said hollows, with the ends of the hollow fibres embedded in said mass of resin material, open ends of the hollow fibres opening on a face of the mass.

In the specification, the expression "hollow fibres" is to be taken to denote fibres of tubular shape, that is to say fibres containing within them a continuous channel which is positioned substantially along the axis of the fibre and which is free from macromolecular material.

The hollow fibres which can be used according to the invention can be of any known type, and in particular they can be the fibres mentioned in French Pat. Nos. 1,307,979, 1,586,563 and 2,017,387 and U.S. Pat. No. 3,674,628; these fibres can be homogeneous or microporous or anisotropic (that is to say "with a skin"). They can be prepared by a melt method, by a dry method (evaporation of the solvent) or by a wet method (coagulation); the spinnerets employed are, in practice, sector spinnerets or spinnerets with an annular orifice. The fibres which can be used according to the invention have an external diameter which is generally between 5 $\mu$ and 1 mm, and preferably between 0.3 and 0.6 mm.

The exact nature of the hollow fibres is chosen as a function of the application considered e.g. gas permeation, dialysis, piezodialysis, thermodialysis, direct osmosis, reverse osmosis, thermo-osmosis, ultrafiltration or hyperfiltration).

The plurality of hollow fibres is usually arranged in the form of a web or of several superposed webs; they can be fibres which are simply placed substantially parallel to one another; they can also be webs in which the hollow fibres are arranged parallel to one another in one and the same web and perpendicularly from one web to the next; finally, these webs can consist of a woven or knitted fabric. In the latter case, the fibres are also substantially parallel to one another, the direction considered for a given fibre being the general direction of this fibre, not taking its curves, twists and local deformations into account. It is also possible to use twisted hollow fibres.

In contrast to the assemblies of the prior art, the primary frames do not have, in their edges, openings or perforations through which fluids can flow. These edges are even preferably solid.

The primary frames can be polygonal and advantageously they are rectangular or square.

The central window of these primary frames can more-over be filled by a perforated element, such as a grid or trellis or grating, which can especially have the role of supporting the hollow fibres in the frame packed with hollow fibres.

The shape of the primary frame, and also of the resin masses, is moreover chosen so that the frames packed with hollow fibres according to the invention can be stacked in a leakproof manner relative to one another. By frames which are leakproof relative to one another there are to be understood frames which (as will be amplified in the following text), in apparatuses for treating fluids, make it possible to distinguish between two zones, one relating to outside the hollow fibres and the other relating to inside the hollow fibres.

The resin masses can consist of a hardened mass preferably of solidified glue) in which the ends of the hollow fibres are embedded, without in any way clogging the central channel of these fibres; these resin masses fix the hollow fibres not only relative to one another but also fix them together relative to the core; from the chemical point of view, this hardened mass is generally solidified glue; as the glue, it is possible to use quick-setting or slow-setting glues, with one or two constituents. Alkyl cyanoacrylates may be mentioned as quick-setting glues and epoxy resins may be mentioned as slow-setting glues, but other glues, such as polyurethane glues, optionally modified by polyisocyanates, as well as silicone-based glues and especially mixtures of triacyloxysilane and diorganopolysiloxane hydroxylic oil and glues as mentioned in particular in French Pat. No. 1,307,979 may be used.

Of course, the resin masses are comparatively thin relative to the length of the hollow fibres (usually less than one tenth of their length) and, together with these hollow fibres, are leakproof relative to fluids.

The primary frames can be made of any solid and leakproof material which is preferably rigid or semirigid. They can be made of metal or preferably of artificial or synthetic polymer. Usually and preferably the material of which the primary frame is made is different from the resin of the plates; it is nevertheless possible that, in some particular cases, it might be necessary to use the same material for the resin masses and the primary frame, but even in this case the resin masses are quite a separate element from the primary frame. In every case, the hollow fibres of course open only at the surface of the masses and not at the surface of the primary frames.

There is also provided, according to the invention fluid treatment apparatus comprising a stack of assembles according to the invention, a container surrounding said assemblies and in fluid tight engagement with the frames thereof, means for feeding a first fluid to said container so that it flows around said fibres and through said windows before leaving the container and means for connecting the interior of the hollow fibres to the exterior of the container.

In order that the invention will be better understood, the following description is given, merely by way of example, reference being made to the accompanying drawings, in which:

FIGS. 11 and 12 represent a fibre assembly including a primary frame equipped with a coil of hollow fibres;

FIG. 13 represents the manufacture of assemblies according to FIG. 11;

Figure 1:
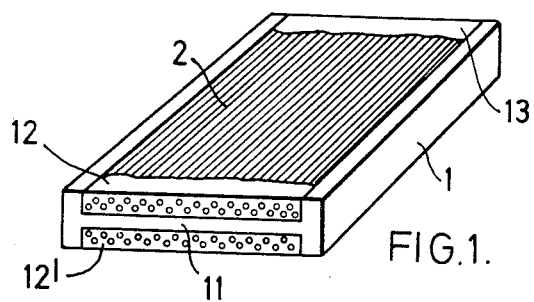
FIG. 1 is a perspective view of one embodiment of assembly according to the invention, the frame being packed with rectilinear hollow fibres which are open at both ends.

FIG. 1 illustrates an assembly including a frame packed with hollow open fibres, the assembly comprising a rectangular primary frame 1 containing two thinned down regions on two opposite sides. In this FIG. 1, only one of the two thinned down sides 11 and 15 is visible, namely the side 11. The thinned down region of this side 11 forms two hollows occupied by the two masses 12 and 12' made of resin. The side 15, opposite side 11, is also thinned down and has two hollows occupied by two resin masses 13 and another mass which is not visible in FIG. 1. The hollow fibres 2 extend from the mass 12 to the mass 13 and from the mass 12' to the said other mass. These hollow fibres 2 are substantially rectilinear and parallel to one another and parallel to two edges of the primary frame 1; they are open at both their ends, these ends being embedded in the various resin masses.

All the edges of the primary frame 1 are solid, that is they do not have any hole or perforation through the thickness of the frame permitting a possible flow of liquid.

Figure 2:
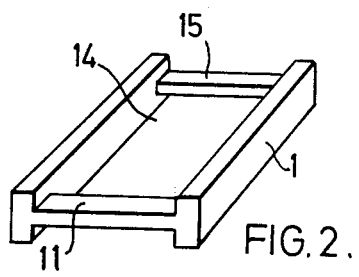
FIGS. 2 and 3 are perspective views of rectangular primary frames with two thinned down regions and four hollows.

The primary frame 1 of FIG. 1 gas been represented in isolation in FIG. 2. This figure clearly shows the two thinned down sides 15 and 11 as well as the central window 14. The thinned down region of each of the sides 11 and 15 is such that the frame possesses four hollows in all.

Furthermore, the two edges of the primary frame which are not thinned down have a surface state which makes it possible to stack these frames, the various juxtaposed edges touching one another.

Figure 3:
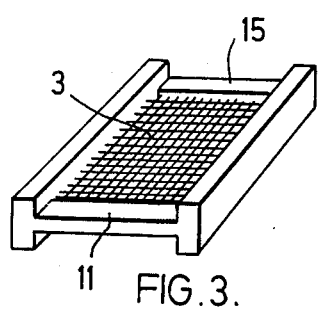

A variant of the primary frame has been represented in FIG. 3, in which the central window 14 is occupied by a perforated element in the form of a grid 3 fixed directly to the edges of the primary frame. This grid makes it possible to support the hollow fibres without having any substantial detrimental effect on the flow of fluid through the frame.

The invention also relates to frames packed with hollow fibres possessing 2 $p$ sides ($p$ is a positive integer, preferably equal to 2), each of these sides being thinned down so as to form 4 $p$ hollows occupied by 4 $p$ resin masses, the hollow fibres being substantially rectilinear, parallel, open at both their ends and extending from one resin mass on one side of the primary frame to the resin mass facing it on the opposite side of the primary frame.

Such frames makes it possible to treat several fluids simultaneously. It is thus possible, in an artificial kidney equipped with such frames, to dialyse two different blood streams with a single dialysis bath.

Figure 4:
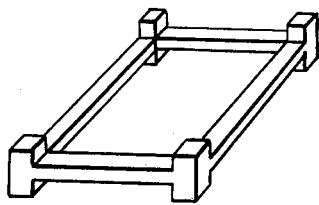
FIGS. 4 and 5 are perspective views of rectangular primary frames with four thinned down regions and eight hollows.

A primary frame which makes it possible to prepare a hollow fibres assembly as has just been described has been represented in FIG. 4. The four sides of this frame are thinned down, thus forming eight hollows. Four parts which have not been thinned down remain at the corners of the frame and they will make it possible subsequently to stack the frames without crushing the hollow fibres. The complete frame packed with hollow fibres has not been represented; the eight hollows are of course occupied by eight resin masses. The hollow fibres, which always extend from one resin mass on one side of the primary frame to the resin mass facing it on the opposite side of the primary frame, can nevertheless be arranged in several ways; they can be arranged in webs of parallel fibres, the fibres of one web being oriented in a given direction (from one side to the opposite side) and the fibres of the adjacent web being oriented in the perpendicular direction (connecting the two remaining sides). The hollow fibres can thus be arranged in alternating webs. It is also possible to use woven webs of hollow fibres, the hollow fibres of the warp then extending between two resin masses situated on two opposite sides, the hollow fibres of the weft extending between two resin masses situated on the other two opposite sides.

The hollow fibres in the form of woven fabrics can also be used with any type of primary frame other than those of FIG. 4. It is possible, for example, to use them with the frames of FIGS. 1 to 3; however, with the frames of FIG. 4, the woven fabrics of hollow fibres can have useful hollow fibres both as the weft and as the warp, while this is not always the case with the frames of FIGS. 1 to 3. For example, if the woven fabric of hollow fibres has its weft and its warp parallel to the sides of the primary frame, the weft (or warp) hollow fibres will end at the resin masses and will thus be useful, whilst the warp (or weft) hollow fibres will not end at any resin mass and will not be useful. In such a case, it will be advantageous either to seal these non-useful warp hollow fibres or to use woven fabrics which have solid yarns as the warp. Another solution consists of arranging the woven fabric of hollow fibres slantwise relative to the sides of the frame. In every case, it is preferable that the fibres which have been rendered non-useful should be sealed or replaced by solid yarns.

Figure 5:
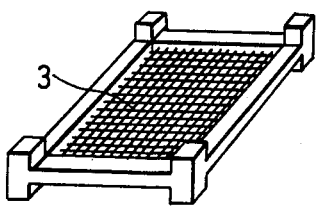

FIG. 5 describes a primary frame similar to that of FIG. 4 but equipped with a grid 3.

Figure 6:
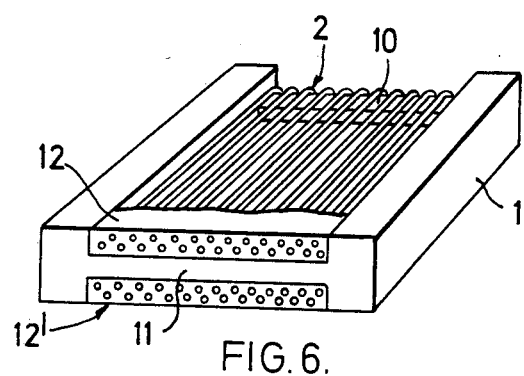
FIGS. 6 to 8 represent a fibre assembly including a primary frame packed with hollow fibres arranged in a U-shape.
Figure 7:
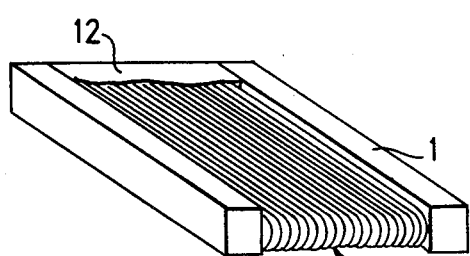
Figure 8:
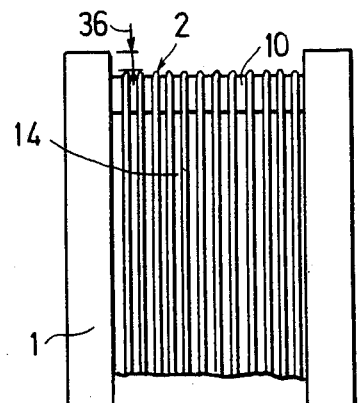

Another type of frame packed with hollow fibres according to the invention, which is of polygonal shape and more specifically of rectangular shape has one side of the primary frame with a thinned down region forming two hollows occupied by two plates made of resin, the hollow fibres being open at both their ends and being substantially U-shaped and extending from one of the two plates made of resin to the other by passing around the edge of the frame opposite the edge carrying the two plates made of resin. According to a preferred embodiment which is represented in FIGS. 6 to 8, the primary frame then simultaneously has a thinned down region and a recess on the edge situated on the side opposite the side equipped with the two plates made of resin. Such frames are more especially suitable for separation operations.

Figure 9:
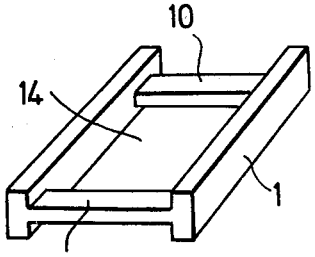
FIGS. 9 and 10 represent two further forms of primary frame with two thinned down regions, four hollows and a recess.
Figure 10:
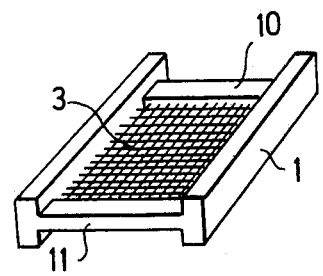

FIG. 6 represents such a frame packed with hollow fibres viewed facing the branches of the U of the fibres; FIG. 7 represents the same frame viewed from the rounded end of the U of the hollow fibres: FIG. 8 also represents the same frame packed with hollow fibres, but viewed from the side, which demonstrates better the recess of the frame which was mentioned above. FIGS. 9 and 10 represent variants of the isolated primary frame used in FIGS. 6 to 8. FIG. 10 differs from FIG. 9 in that the primary frame is equipped with a grid.

More precisely, these frames packed with hollow fibres comprise, as above, a primary frame 1, two sides 10 and 11 of which are thinned down, the side 10 being such that the frame is recessed on this side, as can be seen clearly in FIGS. 8 and 9. The purpose of this recess is to prevent the hollow fibres from projecting beyond the primary frame, since this has advantages when the frames are stacked subsequently.

The thinned down edge 11 has two hollows occupied by the resin masses 12 and 12'. The U-shaped hollow fibres 2 have one of their ends embedded in the mass 12 and the other end embedded in the mass 12'. The rounded part of the U of the hollow fibres passes round the thinned down and recessed side 10.

The primary frame of FIG. 9, as used in FIGS. 6 to 8, has a central window 14 while in FIG. 10, this window is provided with a grid 3.

Figure 20:
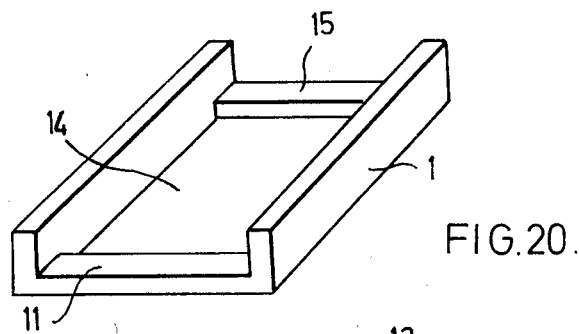
FIG. 20 represents a further form of primary frame with two thinned down regions and two hollows.
Figure 21:
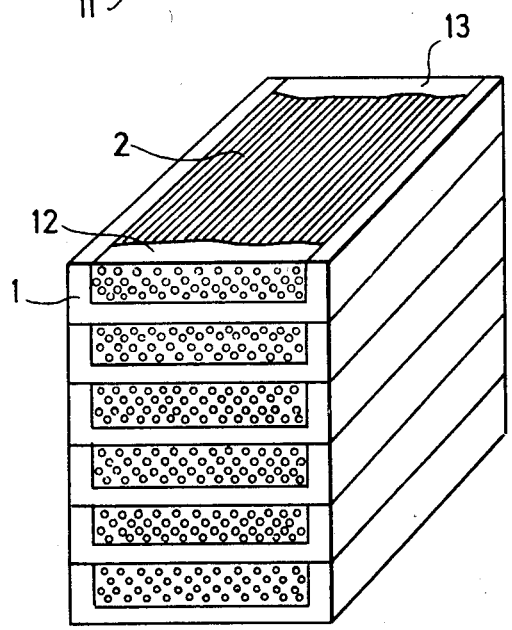
FIG. 21 represents a stack of assemblies each including hollow fibres mounted on a primary frame according to FIG. 20.

In another type of rectangular assembly according to the invention, the two opposite sides of the primary frame each have a thinned down region each of which forms a single hollow, giving two hollows in all, occupied by two resin masses, the hollow fibres being open at both their ends and extending from one of the resin masses to the other. FIG. 20 shows a primary frame which can be used in such frames packed with hollow fibres. FIG. 21 represents a stack of the same frames packed with hollow fibres. The elements of the assemblies in FIGS. 20 and 21 are the same as in the other assemblies, the frame 1 possesses two thinned down edges 11 and 15 and a central window 14. The resin mass 12 occupies the hollow formed at the edge 11. The resin mass 13 occupies the hollow formed by the edge 15 and the hollow fibres 2 extend from the mass to the mass 13.

Figure 22:
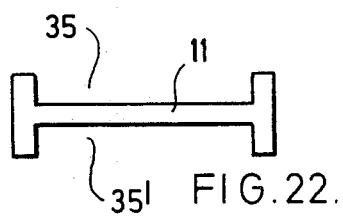
FIG. 22 is an end view of a primary frame according to FIGS. 2 to 5 and 9 and 10.
Figure 23:
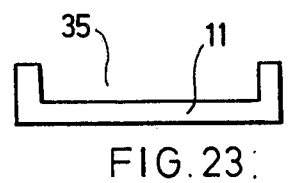
FIG. 23 is an end view of a primary frame according to FIG. 20.

FIG. 22 shows the hollows 35 and 35' of an assembly as in FIGS. 1 to 6 and FIG. 23 shows the hollow 35 of the assembly of FIG. 22. The frame recesses have been shown in FIGS. 8 and 12 under the number 36.

In one method of manufacturing the assembly, the first step is to produce a coil of hollow fibres around at least two opposite sides of a primary frame. The opposite sides of this frame around which the coil is made are preferably the sides which possess a thinned down region and optionally a recess.

Figure 11:
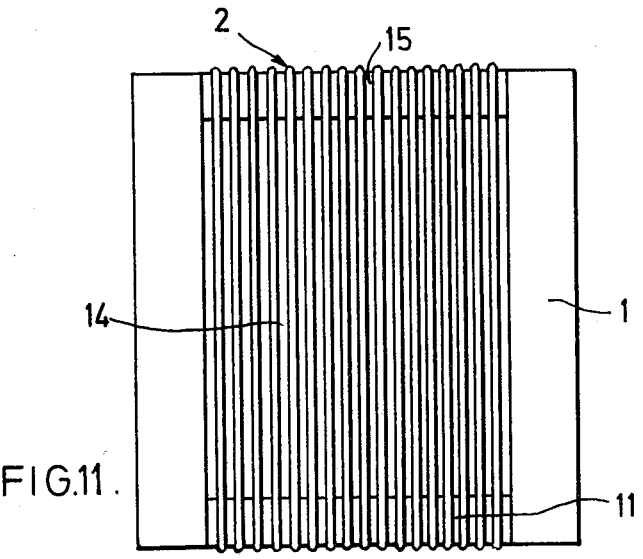

The primary frame 1 provided with the coil of hollow fibres 2 has been represented in FIGS. 11 and 12. In FIG. 11, the primary frame is similar to that of FIG. 2; in FIG. 12, the primary frame is similar to that of FIG. 9. These frames provided with a coil of hollow fibres of FIGS. 11 and 12 make it possible to prepare the frames packed with hollow fibres of FIGS. 1 and 6 to 8 respectively. The coil of hollow fibres in practice constitutes a skein which can be produced by any means which is in itself known.

A method for manufacturing the hollow fibre assemblies is illustrated more specifically in FIG. 13.

This method essentially includes mounting a row of primary frames juxtaposed side by side on a rotating wheel which winds one or more hollow fibres around the said primary frames.

More precisely, the primary frames are juxtaposed and preferably joined, for example, by tabs 4, these tabs fixing the primary frames alternately above and below. Other joining systems can advantageously be used, and especially magnetised pellets embedded in the mass of the primary frame. Whatever the method adopted may be, a line of primary frames which are moved by rolling belts 5 and 5' is obtained in practice. This line of frames passes through the rotating wheel 6 which is caused to move by a transmission system driven from the motor 7. This rotating wheel 6 is held in position by rollers 8, which are themselves supported by the frame 16 of the machine. Furthermore, bobbins of hollow fibres 9 are carried by this wheel 6 and the hollow fibres which issue therefrom pass through yarn guides and are then wound up on the primary frames 1.

Since the web of hollow fibres formed is discontinuous from one frame to another, it is preferable to stop the rotation of the wheel 6 when passing from one frame to another. The way in which the line of frames is supported between the rolling belts 5 and 5' has not been clearly shown in FIG. 13. It is achieved by the proximity of the two rolling belts and by a certain rigidity of the system which fixes the frames to one another.

Once the coil of hollow fibres has been placed in position on the primary frame, it is possible to produce a frame packed with hollow fibres by gluing this primary frame with a resin on at least one of the sides carrying the coil of hollow fibres, and then after this resin has hardened, it is sectioned in such a way as to form resin masses and to open the hollow fibres.

The gluing (or sealing or connecting) can in fact be carried out at the same time as the hollow fibres are being wound on the primary frame. However, in such a case, it is of course preferred to use a quick-setting glue. It is also possible to effect gluing by immersing the end of the frame in a receptacle containing glue; it is possible advantageously to carry out this immersion in a mould made of a flexible material to which the glue does not adhere, for example a mould made of silicone.

After the glue has hardened, release from the mould is effected by any known means. The end of the frame which has been glued by immersion in the glue consists of the side or sides which have been thinned down (but generally not recessed) which are also the sides supporting the coil of hollow fibres.

The sectioning of the glue so as to form the plates made of resin can be effected by any known means and especially by slicing, sawing, planing or cutting. This sectioning is advantageously carried out flush with the surface of the edges of the primary frame.

An advantage of the invention is that the glue does not present the risk of clogging the hollow fibres and that there is no need to take special precautions to prevent this clogging when the gluing is carried out.

A method for the preparation of frames packed with hollow fibres like those of FIG. 21, that is to say frames in which the primary frame possesses two thinned down regions forming two hollows, is characterised in that the following operations are carried out:

α. Hollow fibres are wound around a plurality of primary frames placed on the sides of a rotating polygonal support (preferably with 5 to 20 sides) so as to form a skein holding all the primary frames tightly on the support (the hollows are not positioned against the rotating support but at the outside).

β. The hollow fibres are glued to the primary frame and to one another in the hollows formed by the thinned down sides of the primary frame, this gluing step being concomitant with and/or subsequent to step α).

γ. The hollow fibres are sectioned.

Figure 14:
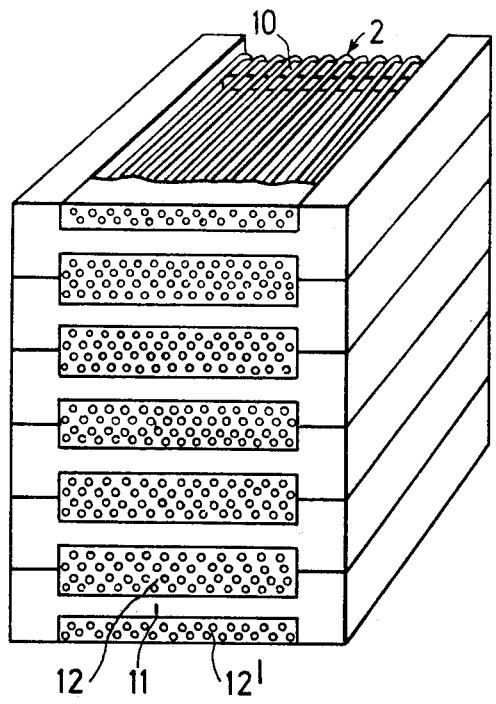
FIGS. 14 and 15 represent a stack of assemblies according to FIG. 6.
Figure 15:
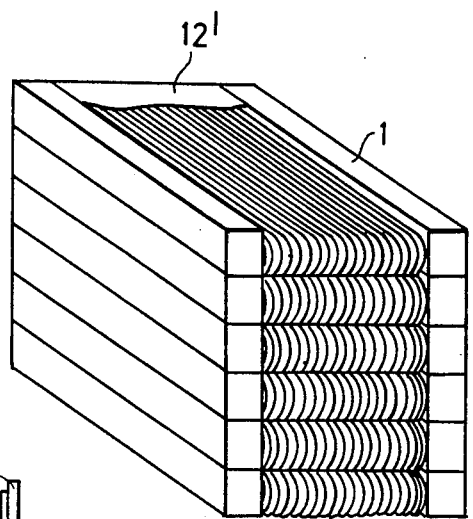

Various stacks of assemblies have been represented in FIGS. 14 to 17 and 21, the assemblies of FIGS. 6 to 8 being shown stacked in FIGS. 14 and 15.

FIGS. 14 and 15 represent the same stack, viewed from the side of the plates made of resin in FIG. 14, and viewed from the side of the rounded part of the U of the hollow fibres in FIG. 15. These FIGS. 14 to 17 and 21 clearly show the way in which the frames and the plates made of resin touch one another. The combination of the leakproof plates and the thinned down edges form a leakproof surface which distinguishes well between the two zones, one relating to inside and the other relating to outside the fibres.

Such stacks of frames, where both ends of the hollow fibres all open into the same zone, are more especially suitable for separation operations (ultrafiltration, reverse osmosis and the like) or also for mixing operations.

These stacks of frames can be formed by simply stacking the said frames and then fixing these frames to one another by gluing. According to more advantageous process primary frames equipped with a coil of hollow fibres as described above are stacked, then gluing is effected, and the resin is cured and sectioned, these last three operations being carried out on the stack of frames and no longer, as before, on a single frame; apart from this, the gluing, curing and sectioning are carried out as indicated above.

It should be noted that the system for fixing the frames to one another by means of tabs 4 situated alternately above and below, as represented in the line of frames of FIG. 13, makes it considerably easier to stack the frames, insofar of course as the said tabs have minimum flexibility, which is practically always the case when they are thin and made of a synthetic macromolecular material. In fact, having produced this line of frames joined by tabs, stacking is effected easily by folding the line like an accordion or in a "zig-zag" manner.

Figure 16:
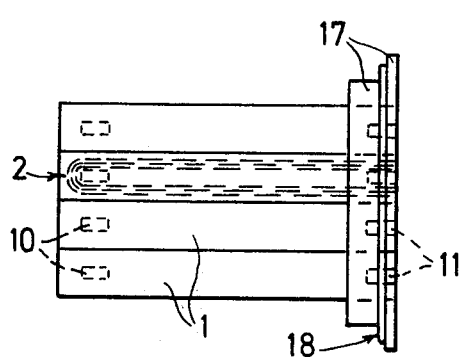
FIG. 16 represents a profile view of a stack such as that of FIGS. 14 and 15 but equipped with a collar.
Figure 17:
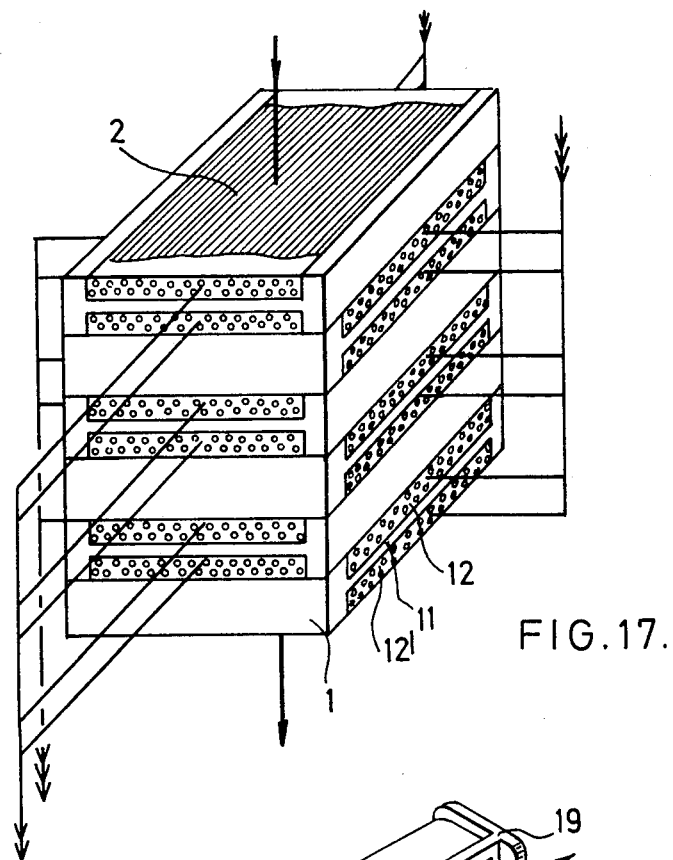
FIG. 17 represents a special stack of assemblies according to FIG. 1.

Other stacks of assemblies according to the invention packed with hollow fibres have been represented in FIGS. 16 and 17. The stack of FIG. 16 differs from those of FIGS. 14 and 15 by the addition of the rimmed collar 17 equipped with the gasket 18. This collar, which grips all the frames, makes it possible to fix the said stack in an apparatus for treating fluids (and does so in a leakproof manner). This will appear more clearly in relation to FIG. 18, where the central detachable element is precisely the stack represented in FIG. 16.

A stack like that of FIG. 16 is formed as indicated for the stacks of FIGS. 14 and 15, the collar and its gasket being preferably placed in position before hardening the glue.

Although the stacking of frames packed with hollow fibres has been described especially in relation to the frames of FIGS. 6 to 8, it is, however, possible to stack any other type of frames according to the invention; thus it is possible to stack the frames in which the hollow fibres are rectilinear (FIG. 1), it being possible for the primary frame itself also to be of any type, and especially of those described in FIGS. 2 and 4.

A stack of frames of the type described in FIG. 1 has been described in FIG. 17, but with the characteristic that the frames are arranged in such a way that two rows alternate uniformly, the frames of one row having their hollow fibres perpendicular to the hollow fibres of the frames of the other row. Other arrangements are of course possible, and especially a stack of frames in which all the hollow fibres are in a parallel arrangement. This special stack of FIG. 17 makes is possible to treat more than two fluids simultaneously, and this has been represented by the system of arrows which illustrate the paths of fluids passing through the stack of frames.

Such an arrangement (FIG. 17) relates essentially to exchange operations and especially to dialysis. This arrangement could also and advantageously be used employing frames packed with crossed hollow fibres like those having primary frames of the type described in FIGS. 4 and 5.

An apparatus for treating fluids using the stack of FIG. 17 would thus comprise three zones corresponding to the three fluids flowing through the apparatus. The first zone corresponds to the fluid, the path of which is represented by an arrow with one arrow head; this zone comprises all the inside of the frames (central window) outside the fibres; the corresponding fluid would sweep over the outside of all the fibres; in haemodialysis, the dialysis bath would be involved.

All the resin masses and the sides of the frames form leakproof surfaces, these surfaces forming a kind of hollow tube with a rectangular, and preferably square, cross-section, the first fluid (arrow with one arrow head) flowing inside the tube. The region outside this hollow tube is further divided into two zones corresponding to the two other fluids passing inside the hollow fibres. One of these fluids, the path of which is represented by arrows with two arrow heads, flows through the hollow fibres of a first row of frames. The other row of frames has hollow fibres perpendicular to the fibres of the first row of frames, and these fibres are traversed by the fluid, the path of which is represented by arrows with three arrow heads.

As has already been stated, all these stacks of frames are only a constituent element of the apparatuses for treating fluids of the invention.

Figure 18:
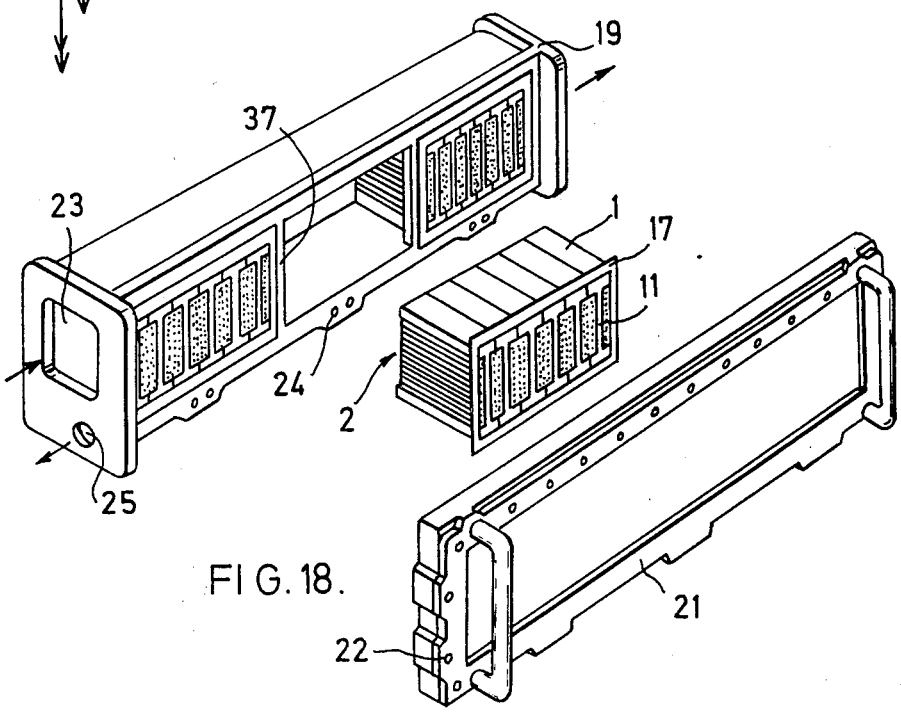
FIG. 18 represents an apparatus for treating fluids using assemblies according to FIG. 6.

A particular example of an apparatus for treating fluids has been represented in FIG. 18. As this apparatus comprises U-shaped hollow fibres and frames packed with hollow fibres of the type described in FIGS. 6 to 8, what is involved more particularly is an apparatus for effecting separation (or also mixing) such as ultrafiltration, reverse osmosis and gas permeation.

More precisely, this apparatus comprises a casing 19 into which several (three) stacks of frames packed with hollow fibres can be introduced, these stacks being equipped with collars 17 as described in FIG. 16. In FIG. 18, two of these stacks of frames have been represented in position in their recess in the casing 19, and the third has been represented outside the casing. The exact shape of the collar 17 is chosen so as to fit into the corresponding recess of the casing 19, the recesses being separated by crossbars 37. The apparatus also comprises a cover 21 which fits over the front of the casing 19, which is equipped with studs which have not been represented but which can be inserted into the holes 22 in order to fix the cover 21 to the casing 19.

The liquid, or more generally, the fluid to be treated is introduced via the inlet passage 23 and sweeps over the fibres, perpendicularly to the hollow fibres as well as to the plane of the frames 1, and through their central windows. It issues again via an opening similar to 23 situated on the other side of the casing 19. The permeate issues from inside the hollow fibres at the front of the casing. The cover 21 provides a chamber which makes it possible to collect the permeate from these various fibres. The permeate issues from this chamber via the pipelines 24 provided in the casing 19. These various pipelines 24 are connected to a single manifold via the opening 25 from which the said permeate issues. Details of the way in which the openings 23 and 25 are joined to the usual connection tubes have not been represented.

The apparatus which has just been described forms a preferred embodiment of the invention. It is clear, however, that the apparatus which has been represented with three stacks of assemblies can have a different number of these; also, each stack of assemblies which has been represented with six frames can also possess a different number of these. Likewise, ribs can serve to strengthen the casing 19 which can have a shape which is different from that represented.

The casing can be closed by any common means other than the studs which have been mentioned.

It has been indicated above that the apparatuses of the invention comprised a container designed to be leakproof relative to the surface or surfaces formed by the plates. It can be seen clearly that in FIG. 18 the container in question consists of the combination of the casing 19 + the cover 21 and that leakproofness is achieved at the level of the collars 17 by means of gaskets 18 which are not visible but which press on the crossbars 37 of the casing 19 and on the casing itself.

The exact configuration of the apparatus for treating fluids will of course have to be modified and adapted as a function of the type of assembly which is chosen and as a function of the type of stack of frames which is chosen, but the general characteristics listed above remain. In every case, leakproofness must be maintained between each of the fluid flow paths, some fluids passing through the central windows outside the hollow fibres and other fluids passing inside the hollow fibres. The latter fluids which pass inside the hollow fibres can, depending on the particular applications considered, either flow through the fibres from one end to the other, or simply (in the case of permeates) flow from inside the fibre to the external recovery compartments (separation operation) or simply enter inside the hollow fibres (mixing operation).

Figure 19:
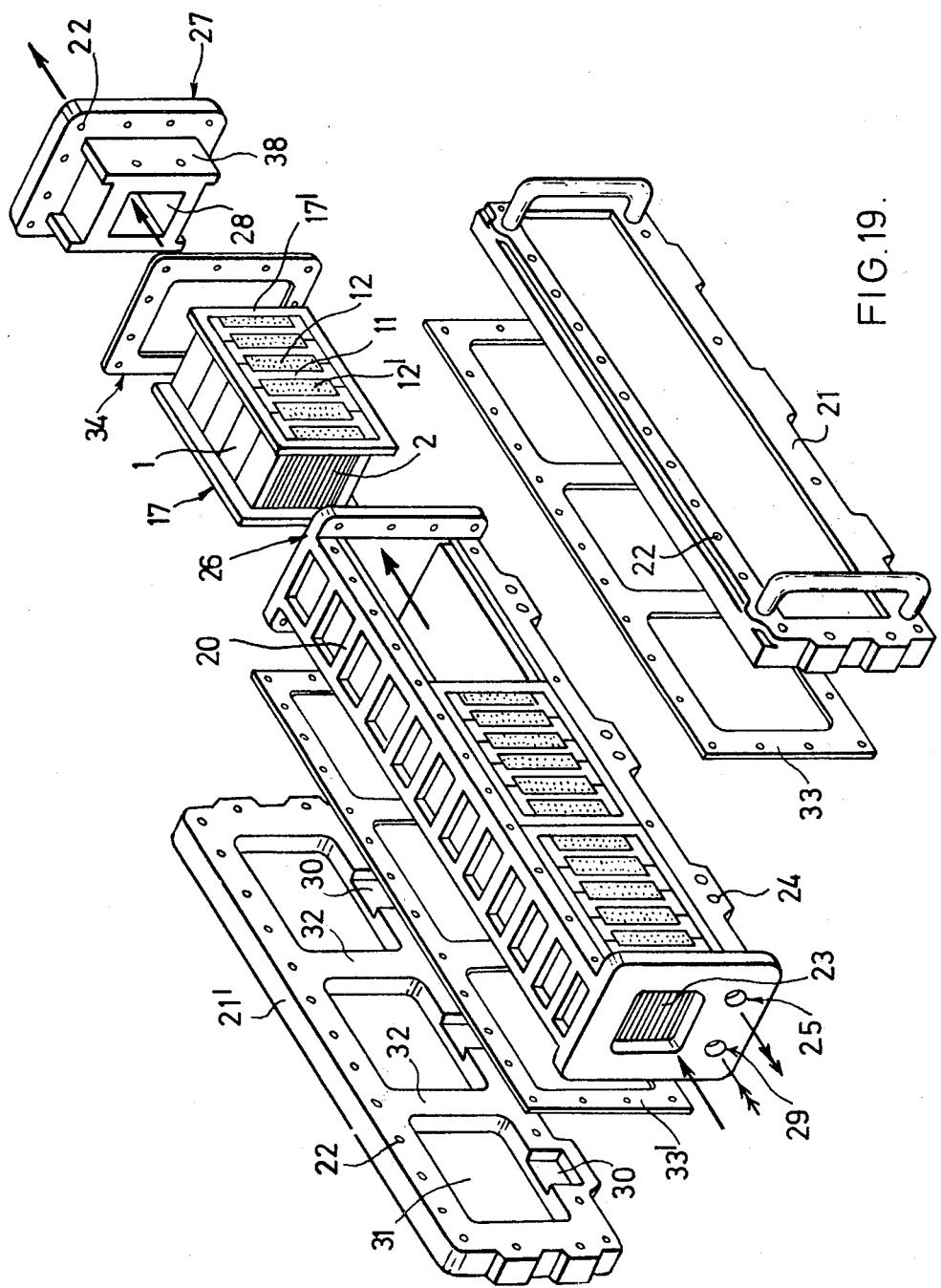
FIG. 19 represents an apparatus for treating fluids using assemblies according to FIG. 1.

An exploded view of another apparatus for treating fluids has been represented in FIG. 19. This apparatus comprises a stack of assemblies of the type of that of FIG. 1, that is to say frames packed with rectilinear hollow fibres which are open at both ends. Such an apparatus is thus more especially suitable for treating fluids employing two different flow paths (exchange operations). The flow paths of these two fluids have been represented by an arrow with a single arrow head in the case of the fluid sweeping over the hollow fibres on the outside (fluid passing through the central windows of the frames). The fluid which flows inside the hollow fibres has its flow path represented by an arrow with two arrow heads.

This apparatus thus comprises a casing 26 which is open on two opposite sides and contains the stacks of assemblies two cover 21 and 21', together with the side plate 27, serve to close this casing. Two stacks of assemblies are represented in position in their recess of the casing and the third is represented out of its recess.

As in FIG. 18, these stacks of frames are detachable. However, whilst in FIG. 18 it was possible to remove them from their recess on the front of the apparatus, in the case of this FIG. 19 and because of the presence of the two collars 17 and 17', the stacks of frames slide into the casing through the side.

The stacks of frames are equipped with two collars 17 and 17' because the hollow fibres are open on two opposite sides of the said frames. Gaskets 33 and 33' are associated with the covers 21 and 21' in order to achieve leakproofness. These gaskets 33 and 33' consist of a rectangular frame equipped with two crossbars, which enables them to press on the front of the stacks of assemblies and more precisely on the various collars of type 17 and 17'. Leakproofness between the two fluid flow paths is thus achieved by tightening the two covers 21 and 21' onto the casing 26 by means of the gaskets 33 and 33'; leakproofness is further achieved at the end of the apparatus by a shoulder 38, firmly fixed to the side plate 27, which presses on the stack of frames, a gasket 34 providing leakproofness between the edge of the side plate 27 and the casing 26. As if FIG. 18, this casing is equipped with studs which are not represented but which correspond to holes 22 both in the covers 21 and 21' and in the side plate 27.

The fluid sweeping over the outside of the hollow fibres thus enters via the inlet passage 23, passing through the various central windows of the assemblies, and issues again via the fluid outlet passage 28. As far as the fluid flowing inside the hollow fibres is concerned, it enters via the passage 29 into a tube which is not visible and which is situated in the casing 26; this fluid then passes through the slots 30 and enters three chambers 31 for distributing fluids which are provided in the cover 21'; the fluid can then pass through the inside of the hollow fibres and can then follow a path identical to that which has been described in FIG. 18. It passes them through the pipelines 24 and issues through the opening 25.

With the apparatus of FIG. 19, there is, as before, a container designed to be leakproof relative to the leakproof surface or surfaces consisting especially of the resin masses; this container is formed by the combination of the casing 26 and the two covers 21 and 21'.

Special apparatuses which make it possible to use the assemblies according to the invention have thus been described in FIGS. 18 and 19. On the basis of the elements thus indicated, other types of apparatuses can easily be produced which make it possible to employ other stacks of assemblies, and especially stacks similar to those of FIG. 17.

We claim:

1. A hollow fibre assembly for use in fluid treatment apparatus, said assembly comprising, in combination:
   a. a primary frame having edges defining a central window;
   b. a thinned down portion of at least two of said edges defining at least two hollows;
   c. a mass of resin material in at least one of said hollows;
   d. a web of hollow fibres extending between said hollows, with the ends of the hollow fibres embedded in said mass of resin material, open ends of said hollow fibres opening on a face of the mass.

2. An assembly as claimed in claim 1, wherein the edges of the primary frame are solid.

3. An assembly as claimed in claim 1, wherein the the edges of the primary frame and of the resin masses have front and rear surfaces, the front and rear surfaces having complementary shapes effective to enable the frames to be stacked in a leakproof manner relative to one another.

4. An assembly as claimed in claim 1, wherein the primary frame is polygonal.

5. An assembly as claimed in claim 4, wherein the primary frame is rectangular.

6. An assembly as claimed in claim 4, wherein the primary frame has two thinned down regions on two opposite faces of opposite edges, to define four hollows occupied by four resin masses, the hollow fibres being substantially rectilinear, parallel, open at both their ends and extending from one mass on one edge of the primary frame to the mass situated facing it on the opposite edge of the same face of the primary frame.

7. An assembly as claimed in claim 4, wherein the primary frame has 2 p edges p being a positive integer, each of these edges being thinned down on opposite faces effective to form 4 p hollows occupied by 4 p resin masses, the hollow fibres being substantially rectilinear, parallel, open at both their ends and extending from one mass on one edge of the primary frame to the mass situated facing it on the opposite edge of the same face of the primary frame.

8. An assembly as claimed in claim 4, wherein one edge of the primary frame has a thinned down region forming two hollows occupied by two resin masses, the hollow fibres being open at both their ends and being substantially U-shaped and extending from one of the two resin masses to the other, passing around the edge of the frame opposite the edge with the two resin masses.

9. An assembly as claimed in claim 8, wherein the primary frame has simultaneously a thinned down region and a recess on the edge situated on the side opposite the side with the two resin masses.

10. An assembly as claimed in claim 4, wherein two opposite edges of the primary frame each have a thinned down region each of which forms a single hollow, the two hollows being occupied by two resin masses, the hollow fibres being open at both their ends and extending from one mass to the other.

11. An assembly as claimed in claim 1, and further comprising a perforated element extending across the central window of the primary frame.

12. An assembly as claimed in claim 1, wherein the hollow fibres are in the form of a woven fabric.

13. A hollow fibre assembly for use in fluid treatment apparatus, said assembly comprising a plurality of frames fixed to one another, each said frame comprising, in combination:
   a. a primary frame having edges defining a central window;
   b. a thinned down portion of at least one of said edges defining at least two hollows;
   c. a mass resin material in at least one of said hollows;
   d. a web of hollow fibres extending between said hollows with the ends of the hollow fibres embedded in said mass of resin material, open ends of said hollow fibres opening in a face of the mass.

14. A hollow fibre assembly as claimed in claim 13, wherein the fibres of all the frames are substantially parallel to one another.

15. A hollow fibre assembly as claimed in claim 13, wherein the frames are divided into two rows, the hollow fibres of one row of frames being parallel to one another and perpendicular to the hollow fibres of the other row.

16. A hollow fibre assembly as claimed in claim 13, and further comprising a collar holding the frames tightly at the level of the resin masses.

17. A hollow fibre assembly as claimed in claim 16, and further comprising a gasket associated with said collar.

18. Fluid treatment apparatus comprising a container, a stack of hollow fibre assemblies located in said container each said assembly comprising, in combination:
   a. a primary frame having edges defining a central window;
   b. a thinned down portion of at least two of said edges defining at least two hollows;
   c. a mass of resin material in at least one of said hollows;
   d. a web of hollow fibres extending between said hollows, with the ends of the hollow fibres embedded in said mass of resin material, open ends of said hollow fibres opening on a face of the mass;

said assemblies being arranged in said container whereby said container is in fluidtight engagement with the frames thereof, means for feeding a first fluid to said container so that it flows around said fibres and through the windows before leaving the container and means for connecting the interior of the hollow fibres to the exterior of the container.

19. Apparatus as claimed in claim 18, wherein the container comprises a casing and at least one cover and the assemblies are arranged in at least one detachable stack.

* * * * *